United States Patent [19]

Boeke

[11] 4,133,732

[45] Jan. 9, 1979

[54] COMBINATION ELECTRODE SYSTEM

[76] Inventor: Jan Boeke, P.O. Box 2327, Chapel Hill, N.C. 27514

[21] Appl. No.: 694,655

[22] Filed: Jun. 10, 1976

[51] Int. Cl.² .............................................. G01N 27/36
[52] U.S. Cl. ............................ 204/195 G; 204/195 M; 204/1 T
[58] Field of Search .............. 204/195 G, 195 M, 1 H

[56] References Cited

U.S. PATENT DOCUMENTS

| | | | |
|---|---|---|---|
| 2,117,596 | 5/1938 | Bender et al. | 204/195 G |
| 2,886,771 | 5/1959 | Vincent | 204/195 R |
| 3,306,837 | 2/1967 | Riseman et al. | 204/195 G |
| 3,700,577 | 10/1972 | Grauer | 204/195 G |
| 3,717,565 | 2/1973 | Doyle | 204/195 G |
| 3,855,098 | 12/1974 | Fletcher | 204/195 G |
| 3,862,895 | 1/1975 | King | 204/195 G |
| 3,880,737 | 4/1975 | Brunt | 204/195 G |
| 3,923,625 | 12/1975 | Fischer et al. | 204/195 G |
| 4,031,606 | 6/1977 | Szonntagh | 204/195 G |

FOREIGN PATENT DOCUMENTS

| | | | |
|---|---|---|---|
| 492936 | 9/1938 | United Kingdom | 204/195 G |
| 495303 | 11/1938 | United Kingdom | 204/195 G |

Primary Examiner—T. Tung
Attorney, Agent, or Firm—Connolly and Hutz

[57] ABSTRACT

The hydrogen ion concentration or pH of liquids may be measured, particularly in industrial or municipal processes, by a combination glass electrode system containing a glass electrode, a reference electrode and a liquid junction connecting the reference electrode with the process liquid. Both the measuring glass electrode and the reference electrode are the same kind of all-solid-state glass button electrodes, electrically connected to an impedance-transforming integrated circuit; all these components being encapsulated in a hermetically sealed shell. The reference electrode is in mechanical contact with a reference gel, external to the sealed enclosure but isolated from the process liquid and in ionic contact with this liquid only at the liquid junction.

12 Claims, 2 Drawing Figures

COMBINATION ELECTRODE SYSTEM

BACKGROUND OF THE INVENTION

Today conventional pH-measurement in industrial processes including water-conditioning and waste-control, is usually performed with a glass electrode combined with a reference electrode and sometimes a thermometric sensor, in a so-called combination electrode or electrode system. This system is then electrically connected through conduits and junction boxes to an amplifier system with read-out and/or recording and controlling functions, in a separate location more easily accessible to controlling personnel. For the measurements thus obtained to be meaningful, the electrode system has to be checked and maintained on a frequent schedule, most times daily, sometimes weekly. Due to the technology of these electrode systems, this maintenance has to be performed carefully by specially trained technicians — a cost factor of pH-control which can be higher than the initial cost of the system itself over the life span of the electrode system, short as that life span may be. Even more disconcerting is the fact that the technology applied in today's electrode systems may lead to sudden, unpredictable breakdown of its pH-reporting function even with a frequent maintenance schedule. Since such breakdown unforeseeably interrupts process control the result will be losses for the manufacturer or, in waste control, pollution problems for the community.

It has therefore, been the object of this invention to reduce the frequency of scheduled maintenance and to virtually eliminate the known sources of unpredictable breakdown. Instead, the electrode system may be expected to work for an extended period without causing losses, until finally gradual symptoms of aging will lead to replacement at one of the scheduled checkups.

SUMMARY

This aim is achieved with minimal replacement expenses for the user of existing pH-control equipment by providing a sealed monolithic design of the complete glass electrode system with a novel design of its essential component parts. It provides the same electrical voltages for pH sensed, as would be the case with a conventional glass electrode system. Additionally, this novel electrode system will, without external temperature correcting means, immediately respond in a self-compensating way to temperature changes of the process liquid and thereby automatically take into account the resulting changes in ionic dissociation of the process liquid — a variable which is ignored by present-day electrode systems. Although the intrinsic value of this electrode system is more than the sum of the improvements in its component parts, the novel components separately may also find use and show improved performance in special installations.

DESCRIPTION OF THE PREFERRED EMBODIMENTS

Figure 1:
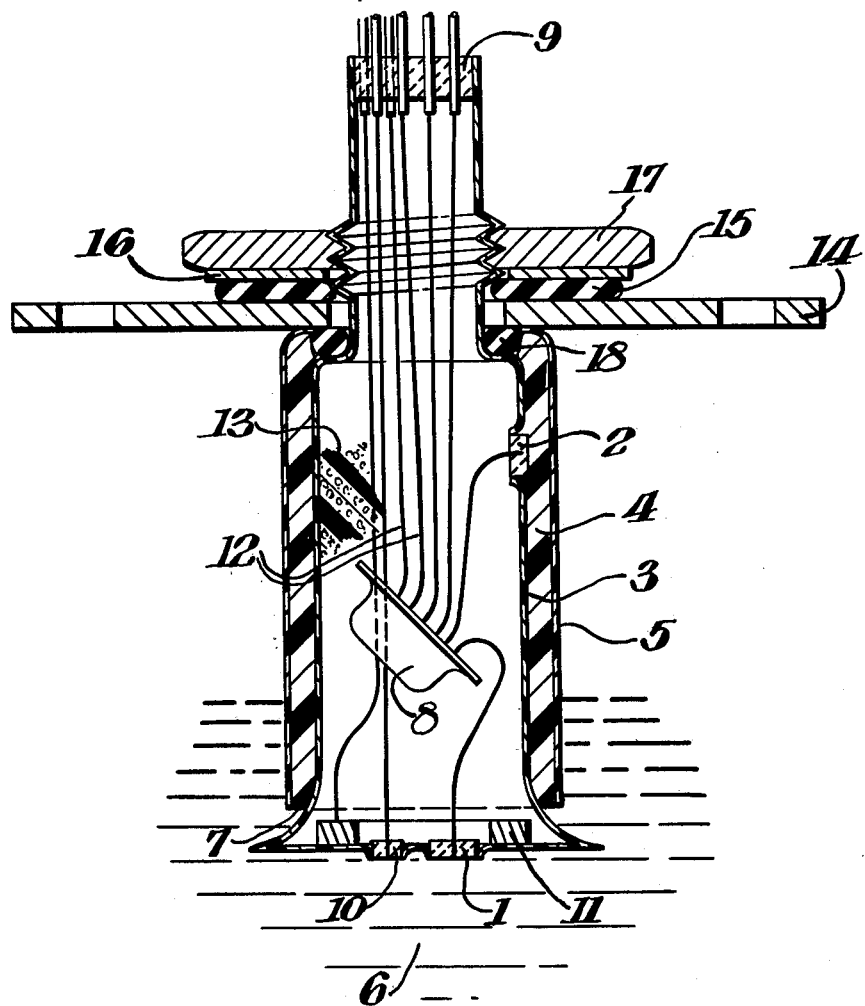
FIG. 1 is a schematic cross-sectional view in elevation of a combination electrode system which is the embodiment of this invention.

The major sources of unpredictable failure of present-day glass electrode systems are:

Breakdown Factor A: Electrical leakage of high-impedance circuit;

Breakdown Factor B: Fragility of the necessarily thin pH-glass membrane.

On factor A: Condensation of moisture or creepage of conducting process liquid between external ground and metal parts directly connected to the output of the glass electrode shorts out the electromotoric force (=EMF) of the glass electrode, since this EMF is developed over the high resistance ($10^8$ to $10^{10}$ ohms, depending on process temperature) of the glass membrane, even though this is kept as thin as is practical. This high source resistance requires an electrical insulation of $10^{12}$ or more ohms of the conducting circuit leading this electrical signal to the pH-amplifier input. Even in cases where a miniaturized amplifier has been built into the electrode system, there is an exposed connector to enable exchange of defective glass electrodes. By necessity this connector is accessible to the hand of the maintenance man, and hence to fatal traces of dirt and moisture. Building the amplifier into the electrode system has here only shortened the length of the high-impedance circuit, but not eliminated the essential possibility for electrical leakage across gaskets and screw threads.

In order to radically cut out all sources of such electrical leakage, the invention provides a water- and vapor-proof permanently sealed enclosure in which both the glass electrode and an impedance-transforming integrated circuit (=ITIC) are hermetically sealed as a monolithic unit. A linear integrated circuit combining the advantages of very high impedance MOS/FET input, single supply capability, small package in a TO-5 can and very low price is the CA3130AT (RCA-numbering) used in the voltage follower mode. Similar in results is the LF155AH (National Semiconductor Corp.) used as a non-inverting unity-gain amplifier, although a moderate amount of gain can be tolerated without loss of input impedance. The circuit which connects the output of this ITIC with the outside world and process-controlling equipment is still susceptible to leakage paths formed by condensate, dirt or creeping solutions as was the electrode output before. But the ITIC has a low output impedance of around $10^3$ ohms or less, and to corrupt this output, leakage paths would have to be of the order of less than $10^5$ ohm. Conventional conduit- and junction-box technology can easily prevent such leakage from occurring, which is a different problem altogether from that of providing a $10^{12}$ ohms insulation for the glass electrode lead against the vagaries of daily inspections by human hands.

The same technique which is used to hermetically seal the glass electrode and its connection to an ITIC can be doubled, with the second glass electrode functioning as a reference electrode. By doing this, a sealed complete combination electrode system can be achieved. Outside the hermetic enclosure the reference electrode is in liquid contact with a gelled reference liquid, i.e. an ionic medium of known pH, which known pH is the reference.

In conventional glass electrode systems and combination electrodes, the reference electrode is usually a metalmetalchloride system where the metal chloride is to a high degree insoluble, built into a reference cell containing a potassium chloride solution of specific strength. This solution is in liquid or ionic contact with the process fluid through a so-called "liquid junction" which may be a fine channel, a slit, a porous medium filled with the potassium chloride reference liquid, or gelled reference liquid. Reference cells of this type, surrounding the stem of the glass electrode in a concentric manner, and with junctions encircling the pH-sensitive glass measurement membrane, are well known. However, the use of the process liquid itself, brought to its desired endpoint pH, as a reference liquid for a solid-state glass electrode as reference electrode, used with a similar solid-state glass electrode as pH-measurement electrode is novel and has several unique advantages.

If now, during process control the process liquid is brought to its proper pH endpoint, we will have, at this moment of correct endpoint, at the electrode system the following potential-forming chain:

Process fluid at endpoint pH/measuring glass electrode/input of ITIC/reference glass electrode/gelled endpoint-pH process fluid.

This chain is fully symmetrical, hence should have zero volts output. More important: it will have this output at any process temperature, regardless of the changes in absolute pH of the fluids involved due to changes in temperature-dependent ionic dissociation equilibria. At every process temperature, the manufacturer will be assured that at zero volts output of the electrode system, the process fluid has the same composition, pH-wise, as the ideal endpoint fluid prepared in his lab. Deviations from zero volts output clearly and unambiguously indicate that the process liquid is not (yet) at its desired endpoint and requires further pH-control.

Gelling of the reference liquid can be achieved by adding fumed silica or carboxymethyl cellulose or any other practical gelling agent to the reference liquid. In those installations where it is more desirable to have an output of zero volts at pH 7, as is common with many electrode systems today, a gelled buffer of pH 7 can be used as a reference gel. At any pH-value outside of that of the reference gel, the EMF produced by this combination electrode system will be identical to the EMF produced by a conventional electrode system.

Every reference liquid has to have unimpeded ionic contact with the liquid to be measured. Usually this contact is provided by a potassium chloride (=KCl) solution of specific strength. So-called "sealed reference electrodes" utilizing gelled KCl-solutions and a stationary junction have been used, but it will be clear that here dilution and contamination of the KCl-gel by the process liquid is just a matter of time. With this system, using a gelled process fluid of endpoint pH, such dilution or contamination is impossible, since on average the process fluid under pH-control measured at the electrode system, will have the same composition as the reference fluid; plus or minus deviations in pH average out. This desirable condition and the symmetrical potential-forming chain are only possible with this electrode system, using glass electrodes for both measurement and reference. This is a basic difference from the asymmetrical electrode chain conventionally used, with a reference cell filled with KCl-solution. The most desirable aspect of this electrode system with two glass electrodes, however, is that it enables one to provide a hermetically sealed combination electrode with extended service life, and to eliminate the earlier mentioned Breakdown Factor A: Electrical leakage.

In order to eliminate Breakdown Factor B: Applicant has resorted to a novel form of glass electrode. The conventional glass electrode consists of a thin-walled glas bulb of pH-sensitive glass, filled with a specific reference solution in which is mounted an internal reference electrode, usually consisting of a wire stub with a silver-silversalt coating. This construction is necessarily fragile. Efforts to free the user from the restraints of a liquid-filled bulb are old (see Bender & Pye, U.S. Pat. No. 2,117,596 of May 17, 1938), and many forms of glass electrodes with metal electrode contacts have been developed since. Although the fragility of the liquid-filled bulb may have been avoided, these constructions carry the causes for two other kinds of fatal and unpredictable failure. Due to the difference in thermal expansion between the metal of a plate or disc used as electrode contact, and the pH-sensitive glass, tensile stresses may be set up in the glass which at an unpredictable moment may lead to one or more hairline cracks. Moisture creeping into such a crack shorts out the high electrical resistance of the EMF-determining glass skin, and makes pH-measurement erratic or meaningless. Efforts to cushion these stresses by using a sequence of glass layers with graded thermal coefficients of expansion introduces still another cause for hairline cracks. pH-sensitive glass is always somewhat water-absorbent, which leads to a certain amount of swelling of the glass. The next layer of glass, with a different composition, may also have a different absorbency for water and a different rate of swelling, which again may lead to fatal tensions.

Although any of these "solid-state" glass electrodes may be used with this novel sealed electrode system, applicant has developed a solid-state glass electrode (= Button electrode) which avoids the above causes of unpridictable failure and of a second category which has received little attention sofar but is just as unpredictable and pernicious to an industrial electrode system with a longer projected service life: erratically shifting assymmetry potentials which add on to the legitimate pH-potentials. By taking care of an even and intentionally well-defined distribution of mobile ions at the glass-metal interface during manufacture by steps to be discussed further down, this problems has been solved by producing a glass electrode which is particularly well adapted to the construction of this combination electrode system. This system, incorporating the button electrodes, is shown in FIG. 1. Here the measurement glass electrode button 1 and the reference glass electrode button 2 are sealed into shell 3. This shell may be made of plastic, enameled steel or stainless steel coated with an insulating coating wherever the shell is in contact with gelled reference solution 4, contained between shell 3 and the mantle 5 whch may be made of the same or another material as the shell as long as the mantle isolates the reference gel electrically from the surrounding process liquid 6 except for seam 7 which forms an ion-permeable junction between reference-and process-liquids.

The electrode leads of both measurement glass electrode 1 and reference glass electrode 2 are directly and permanently connected to the highly isolated, high input resistance floating inputs of ITIC 8. Usually such an IC has provisions for driving a guard shield. This output may be connected to a metal wire sleeve (not shown) surrounding the leadwire between measurement electrode 1 and ITIC input, and to screen off the back of the glass electrode. However, this precaution is not essential in our construction.

The outputs of ITIC 8 and service connections for electrical supply, instrument ground etc. designated 12, are connected to the inside of the pins of sealed-on cable connector 9. A platinum or gold redox electrode 10 for additonal measurement of redox potentials, using the reference glass electrode for reference, may also be sealed into the shell by way of an insulating seal, and internally connected to a separate pin of cable connector 9.

In order to keep the measuring glass electrode and the junction seam clean and in unobstructed contact with the process fluid, a piezo-electric transducer 11 may be mounted inside the shell, with internal electrical connections to pins of cable connector 9. The transducer may provide ultrasonic or vibration cleaning of the active areas. Conventional glass electrode systems never allow close mechanical contact between the transducer and the glass electrode since the strong vibrations may strip the coating off the internal reference electrode inside the glass electrode. The solid-state button glass electrodes, however, are not sensitive to this effect, nor do they have the built-in stresses in the glass which may be triggered by the vibration into forming hairline cracks.

Before final sealing of shell 3, it is filled with potting compound, polymerizing monomer or foam fill 13. Right before local installation, the space between mantle and shell may be filled with reference gel particular to the local application, and closed with O-ring 18. Installation may be done with a demountable mounting flange 14, held by a gasket 15, washer 16 and retainer nut 17. It may be advantageous for reducing electrical noise pickup to fabricate the mantle of non-corroding metal, and to ensure that it has metallic contact with the metal wall of the vessel on which the system is mounted, or with earth ground, so that it may act as a shield. It is essential however, that the inside of the mantle be coated with an insulating coating to avoid direct electrical contact between the mantle and the reference gel.

Figure 2:
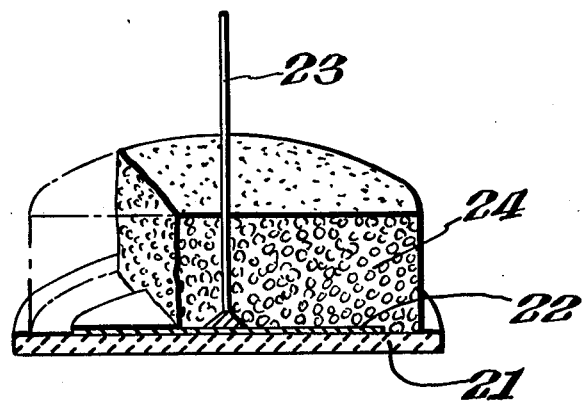
FIG. 2 is a three-dimensional view in cross section and partly broken away of a button glass electrode of this invention.

The construction of the button glass electrode is shown in FIG. 2. A disc 21 of pH-sensitive glass is centrally covered by a metallic or otherwise conducting electrode contact 22. Under the influence of the hydrogen ion concentration in the liquid adjacent to the glass surface, ions will travel through this glass disc and transfer their charge to the electrode contact 22. This again will give rise to an electron current travelling through leadwire 23 to the ITIC 8 of FIG. 1.

In order to prevent the build-up of spurious polarization or asymmetry potentials between electrode contact 22 and glass disc 21, the interface between disc and contact is during manufacture charged with a specific concentration of ions which have a measurable mobility in the glass matrix, like silver (=Ag) ions. This can be achieved by either providing a uniform thin layer of a silver compound like $Ag_2S$ or $Ag_2SO_4$ between contact and glass, or by using a contact made of or coated with metallic silver, and during manufacture electrolyzing silver ions into the glass at a higher temperature. This may be done by making leadwire 23 positive with regard to a layer of graphite powder on which glass disc 21 is resting, and passing through this assembly a predetermined amount of coulombs of electrical charge over a predetermined span of time at a predetermined temperature. This way, always the same number of silver ions will be driven to the same depth into the same area of glass, resulting in a uniform contact potential in all electrodes manufactured. The amount of coulombs to be passed through should be selected such that it exceed by at least a factor 100 the number of coulombs expected to pass through the electrode (worst case) during its lifetime of pH-measurement or -reference.

Not to increase excessively the electrical resistance of the pH-sensitive glass disc, its thickness will be held relatively thin, but still appropriate in view of abrasion or erosion during a reasonable lifetime. The necessary strength to eliminate fragility is obtained by backing the disc pluscontact assembly with a heavy layer 24 of open-sintered coarse glass granules. It is this porous glass backing which will provide anchoring of the button in the electrode holding shell 3 of FIG. 1, should a shell of preformed plastic, or of a compound cast around the essential components or polymerized in place, be used. For sealing the buttons in a metal shell, conventional glass-to-metal sealing techniques may be used. But in both cases, the porous structure of the backing will absorb any stresses caused by the sealing process rather than passing them along to the pH-sensitive glass disc where they might cause hairline cracks.

In an effort to consistently remove all causes of unpredictable electrode failure by hairline cracks, applicant has resorted to the use, for electrode contact, of soft, yielding metals like annealed copper or silver, in the form of thin foils, wire screens or as shown in the example, as a thin, spongy disc. Leadwires should also be soft and thin, so that they will yield rather than set up stresses in the glass.

For the same reason, the use of different glasses with different coefficients of expansion for faceplate and for backing should be avoided. It may be practical to use for porous backing a glass with a lower softening point than the pH-sensitive face plate.

A practical example will be given for the fabrication of button electrodes according to the description:

A thin homogeneous paste is made by ball-milling silver oxide with a predetermined few percent of silver sulfate or silver sulfide and a selected amount between 10 and 40% of the fine glass powder used in the next step. The liquid phase in this paste may be water with a binder like carboxymethylcellulose, or benzene with polystyrene, or any other suitable vehicle. With silk-screen printing techniques, discs of a uniform diameter of 15mm are printed on ashfree filter paper in a widely spaced dot pattern, and dried. Well centered, on top of the discs, is printed a pattern of larger diameter discs of a fine powder of pH-sensitive glass suspended in a similar vehicle as used in the previous step. The thickness of the glass powder discs is considerably more than that of the silver compound discs, and should be such as to yield in the final button a pH-sensitive faceplate of appropriate thickness. This thickness is to be held as uniform as possible. After drying, the sheet with the composite printed-dot pattern is clamped between two flat graphite slabs with spacers of about the thickness of the printed dot. This assembly is slowly heated in a furnace in air up to about 400° C., until all the filterpaper has burnt away and the silver oxide is reduced to silver; and then continued in a neutral or slightly reducing atmosphere (to prevent undue oxidation of the graphite) up to a temperature where the glass powder fuses to a non-porous disc, but below the melting point of the silver or its compounds. Upon cooling and taking apart, a collection of pH-sensitive glass discs with electrode contacts will have been obtained. Now thin silver lead-wires are mounted on the electrode contacts with a silver oxide paste, and in a graphite mold a cylinder of coarse glass powder is filled on top of each electrode contact. This assembly is heated to a suitable temperature well below the melting point of silver or the softening point of the pH-sensitive glass, but above the dissociation temperature of silver oxide until the glass powder is fused or sintered into a solid but open-pored block, as is done in the fabrication of sintered-glass filters. Such a loosely sintered mass behaves somewhat like foam-rubber. Stresses exerted upon it are cushioned and absorbed. This is the case with stresses caused due to differences in thermal expansion as well as due to difference in water absorption of the glass, or stresses caused by a solidifying surrounding polymer. As a result, the solid pH-sensitive glass face-plate is not subjected to potentially fatal stresses, as it would be if the adjacent glass were not porous but solid. This also applies to a face-plate of other ion-specific material.

This heating operation may be combined with the controlled electrolysis of the silver compound as described earlier. This finishes the fabrication of the button electrodes.

A combination electrode assembly in a sealed shell may now be fabricated by placing in a mold the necessary component parts with the button electrodes in recessed cavities. The ITIC's are wired to the electrodes and the cable pins, and so located in the mold that their cans touch the mold walls or fit into shallow recesses. The mold is now filled with polymerizing closed-cell foam or silicone or other potting compound with high electrical insulation value and excellent water-resistance. Upon solidification a core is obtained which holds all component parts embedded and which will be referred to as "the assembly".

This assembly is then placed in a wider mold and a suitable epoxy compound or other polymerizing or congealing fluid poured around the foam core to form the hermetically sealing shell. Particular care should be taken that the button electrode faces remain exposed, but polymer compound should sufficiently penetrate the porous backing of the buttons and seal off the electrode contact and lead wire in a water- and vaporproof manner.

The ITIC-cans may have to dissipate a small amount of Joule heat during use. For good thermal contact to the outside world, they should touch, or preferably be partly embedded in, the outer shell without becoming exposed to the outside of the shell.

It may be clear that by substituting ion-specific glass or ion-specific compounds instead of pH-sensitive glass, ion-specific button electrodes can be manufactured. In combination with either an ion-specific or a pH-specific reference, combination electrode assemblies can be made which are ion-specific and may have automatic compensation for undesired pH-dependence as may be the case with redox potentials.

Electrically, the built-in ITIC may be biased to show a "live zero" of predetermined magnitude at the process endpoint to produce a one-way-going or single-polarity control signal as is often used.

Instead of encasing only one pH-measuring electrode button in the shell, it has unique and novel advantages to encase three or more separate and independent pH-measuring electrode buttons, each connected to its own ITIC input, but sharing the reference. An appropriate external comparator circuit will continually or intermittently monitor the measured-pH outputs and decide whether all measuring electrodes produce the same voltage with regard to the reference. As soon as one electrode starts to deviate within certain norms from the "majority" of remaining equal-potential indicating electrodes, an alert will be given so that the complete combination electrode system may be exchanged for a fresh one at a convenient moment. In the meantime, the "majority" will keep the process under proper control until combination-electrode-replacement, without risks or economic losses due to off-specification operation. Although more measuring electrodes may be used, even a triple-electrode combination electrode system will completely eliminate unpredictable breakdown of the system, yet be not any bulkier nor any costlier than present-day combination electrodes in industrial holders.

Although it will always be possible to correct externally, in the control room, for experimentally measured differences in offset-voltages of ITIC's or electrode buttons, my two-step method of fabrication is particularly advantageous since the assembly, obtained after the first step, can now be tested during manufacture for voltage-offset between duplicating electrode buttons and their ITIC's. These offsets can usually be adjusted with small potentiometers wired to the ITIC according to instructions by their manufacturer and embedded in the central core in such a way that adjustment of these potentiometers is still possible. After adjustment, the whole assembly is encapsulated in the outer shell as already described. No handling of the sealed unit can now disturb the proper offset adjustments, and true exchangeability between combination electrode systems is insured, provided their reference pH is the same.

Internal offset-correction may also be of value for single-measurement-electrode systems, to insure proper potential difference between reference and measurement electrode with their associated ITIC's and to eliminate pre-application calibration by the user except for the most exacting applications.

I claim:

1. A device for sensing ions in liquids comprising a sealed receptacle having an outer wall, an outer shell disposed partially about the receptacle and distanced therefrom to provide a space therebetween, part of the outer wall being outside of the space, a reference solution disposed in the space, an ion-permeable seal on the space for retaining the reference solution while permitting it to be disposed in ion-permeable contact with a liquid to be tested, a pair of openings in the wall of the receptacle, one of the openings being connected to the space and the other of the openings being disposed in the part of the wall outside of the space for contact with the liquid, a pair of solid state ion-sensitive electrodes being mounted in the openings whereby one of the solid state ion-sensitive electrodes is in ionic contact with the reference solution within the space and the other is adapted for ionic contact with the test liquid, an impedance transforming integrated circuit member having a high input impedance and a low output impedance disposed within the receptacle, and the member being connected between the solid state ion-sensitive electrodes whereby the ions in the liquid to be tested are measured by comparison of the signals derived from the solid state ion-sensitive electrodes and the exposure of high impedance components to leakage is minimized.

2. A device as set forth in claim 1 wherein the solution is gelled.

3. A device as set forth in claim 1 wherein a number of impedance transforming integrated circuit members and connected solid state ion sensitive electrodes are provided whereby accurate operation of the device is prolonged.

4. A device as set forth in claim 3 wherein at least three members and connected solid state ion sensitive electrodes are provided.

5. A device as set forth in claim 3 wherein the solid state ion-sensitive electrode contacting a separate reference solution has an ion-sensitivity different from that of the ion-sensitive electrode contacting the liquid to be tested.

6. A device as set forth in claim 1 wherein each of the solid state ion-sensitive electrodes comprises a porous glass backing to minimize stresses applied to the electrodes.

7. A device as set forth in claim 6 wherein each of the solid state ion-sensitive electrodes has soft yielding metal parts to minimize stresses.

8. A device as set forth in claim 7 wherein there is an interface between each of the solid state ion-sensitive electrodes and the soft yielding metal parts, and ions of measurable mobility are disposed contiguous to the interface.

9. A device as set forth in claim 7 wherein an auxiliary opening is provided in the wall of the receptacle outside of the space and an auxiliary electrode is mounted in the auxiliary opening.

10. A device as set forth in claim 1 wherein the receptacle is cylindrical, the outer shell comprises a cylinder slightly larger than the receptacle, leaving a slight annular space between the recepticle and outer shell and an ion-permeable seal is provided in the slight annular space.

11. A device as set forth in claim 1 wherein the solid state ion sensitive electrodes comprise solid state glass electrodes.

12. A device as set forth in claim 1 wherein the reference solution is a test liquid brought to a desired endpoint.

* * * * *